US012605210B2

(12) United States Patent　　　　　(10) Patent No.:　US 12,605,210 B2

Wei et al.　　　　　　　　　　　　　(45) Date of Patent:　Apr. 21, 2026

(54) SYSTEM AND METHOD FOR PLANNING SURGICAL RESECTION OF LESIONS BY A LINEAR CUTTING STAPLER

(71) Applicant: EDDA TECHNOLOGY, INC., Princeton, NJ (US)

(72) Inventors: Guo-Qing Wei, Plainsboro, NJ (US); Cheng-Chung Liang, West Windsor, NJ (US); Xiaolan Zeng, Princeton, NJ (US); Li Fan, Belle Mead, NJ (US); Jianzhong Qian, Princeton Junction, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 1021 days.

(21) Appl. No.: 17/771,324

(22) PCT Filed: Oct. 23, 2020

(86) PCT No.: PCT/US2020/057201

§ 371 (c)(1),
(2) Date: Apr. 22, 2022

(87) PCT Pub. No.: WO2021/081433

PCT Pub. Date: Apr. 29, 2021

(65) Prior Publication Data

US 2022/0378507 A1　　　Dec. 1, 2022

Related U.S. Application Data

(60) Provisional application No. 62/924,972, filed on Oct. 23, 2019.

(51) Int. Cl.
*A61B 34/10*　　　　(2016.01)
*A61B 17/072*　　　(2006.01)
(Continued)

(52) U.S. Cl.
CPC ............ *A61B 34/10* (2016.02); *A61B 17/072* (2013.01); *A61B 17/07207* (2013.01); (Continued)

(58) Field of Classification Search
CPC . A61B 34/10; A61B 17/072; A61B 17/07207; A61B 2034/105; A61B 2034/107; G16H 30/20; G16H 30/40
See application file for complete search history.

(56) References Cited

U.S. PATENT DOCUMENTS 8,484,001 B2　7/2013　Glozman et al.
9,237,891 B2　1/2016　Shelton, IV
(Continued)

FOREIGN PATENT DOCUMENTS

CN　　　2857869 Y　　1/2007
CN　　101742972 A　　6/2010
(Continued)

OTHER PUBLICATIONS

Extended European Search Report issued Oct. 13, 2023 in EP Application No. 20878338.1.
(Continued)

*Primary Examiner* — Brian W Wathen
(74) *Attorney, Agent, or Firm* — Venable LLP

(57) ABSTRACT

A method, system, medium, and implementations for computer-aided preoperative surgical planning are described. Input data acquired with respect to a part of a patient is received by the system. The part corresponds to an organ, e.g., lung, of the patient to be operated on and includes one or more lesions to be removed during an operation. Then, an anatomic 3D model of the part of the patient is generated. Based on the generated anatomic 3D model, a preoperative plan for linear-cutting stapler resection of the one or more lesions from the organ to be carried out during the operation
(Continued)

is obtained. The stapler cartridge size and the staple length are estimated based on the preoperative plan. Further, the resection based on the preoperative plan is visualized.

18 Claims, 17 Drawing Sheets

(51) Int. Cl.

| | | |
|---|---|---|
| *G16H 30/20* | (2018.01) | |
| *A61B 17/00* | (2006.01) | |

(52) U.S. Cl.

CPC .... *G16H 30/20* (2018.01); *A61B 2017/00809* (2013.01); *A61B 2017/07271* (2013.01); *A61B 2017/07285* (2013.01); *A61B 2034/105* (2016.02); *A61B 2034/107* (2016.02)

(56) References Cited

U.S. PATENT DOCUMENTS

| | | | |
|---|---|---|---|
| 9,572,577 | B2 | 2/2017 | Lloyd et al. |
| 10,679,417 | B2 | 6/2020 | Wei et al. |
| 10,828,030 | B2 | 11/2020 | Weir et al. |
| 2016/0128782 | A1 | 5/2016 | Wei et al. |
| 2018/0085079 | A1* | 3/2018 | Krimsky ................ A61B 34/10 |
| 2018/0085169 | A1 | 3/2018 | Krimsky |
| 2018/0116726 | A1* | 5/2018 | Liang .................... G06T 19/006 |
| 2018/0161102 | A1* | 6/2018 | Wei ........................ A61B 34/10 |
| 2019/0192150 | A1* | 6/2019 | Widenhouse ...... A61B 17/3403 |
| 2019/0192227 | A1* | 6/2019 | Shelton, IV ..... A61B 17/07207 |
| 2020/0035348 | A1* | 1/2020 | Sartor .................. A61B 90/361 |
| 2020/0246073 | A1 | 8/2020 | Rossetto et al. |

FOREIGN PATENT DOCUMENTS

| | | |
|---|---|---|
| CN | 105147416 A | 12/2015 |
| RU | 2170547 C1 | 7/2001 |
| WO | 2015169058 A1 | 11/2015 |
| WO | 2019186500 A2 | 10/2019 |

OTHER PUBLICATIONS

International Search Report and Written Opinion mailed Jan. 8, 2021 in International Application No. PCT/US2020/057201.

Notice of Allowance issued on Jul. 16, 2024 in Chinese Patent Application No. 202080086010.5.

Extended European Search Report dated Sep. 19, 2025 in European Patent Application No. 25 17 0566.

\* cited by examiner

310

320

330

340

Initialize the system

Generate an anatomic 3D model based on image data of the patient

Plan the shape, size, position and orientation of wedge resection

Render the planning results to the user in an intuitive way

300

510 Receive image data of the patient

520 Estimate lung segment(s) based on division model(s)

530 Localize lesion(s) within the divided lung segment(s)

540 Identify other anatomies of interest

550 Build an individualized 3D model for the patient

560 Output the built individualized 3D model

500

1210

Receive the determined details of wedge resection

1220

Calculate relevant parameters of the planned wedge resection

1230

Estimate parameters of linear cutting stapler(s)

1240

Generate a visualization signal for rendering

1250

Output the generated visualization signal

1200

SYSTEM AND METHOD FOR PLANNING SURGICAL RESECTION OF LESIONS BY A LINEAR CUTTING STAPLER

CROSS-REFERENCE TO RELATED APPLICATIONS

The present application is a U.S. National Stage Application under 35 U.S.C. § 371 of International Patent Application No. PCT/US2020/057201, filed on Oct. 23, 2020, which claims priority to U.S. Provisional Patent Application 62/924,972, filed Oct. 23, 2019, the contents of which are incorporated herein by reference in their entireties.

BACKGROUND

1. Technical Field

This disclosure relates to computer-aided medical procedures.

2. Technical Background

In recent decades, the ubiquitous presence of the Internet and data access in electronic forms have facilitated advancement of various technologies, including big data analytics and machine learning. Artificial intelligence (AI) technologies have been applied to computer aided medicine, including in surgical planning based on big data and machine learning. For example, machine learning techniques have been used for generating a realistic 3D model of a patient's anatomy from CT/MRI scans and X-ray images based on historic data. In recent years, medical professionals have used such a computer-generated 3D model as a visual aid to plan medical procedures so that real operations can be made more accurate and target driven. For an example, by drawing on a computer cut lines and drill paths on a model for a part of a human body to be operated on, a surgeon can visualize the procedure prior to the procedure. The typical goal of preoperative surgical planning may also be used to identify the accurate 3D position where a lesion is localized and accordingly determine where cutting lines should be in the operation.

Due to its minimally invasive nature, Video Assisted Thoracic Surgery (VATS) has become widely adopted in a variety of operations such as thoracic operations. For an example, with the aid of a special video camera called a thoracoscope, healthcare providers may perform a wedge resection (removal of a lesion such as a cancerous tumor or a suspicious nodule, as well as a wedge-shaped section of the healthy tissue around the lesion), a segmentectomy (resection of one or more pulmonary segments), a lobectomy (removal of one or more pulmonary lobes of the lung), or a pneumonectomy (removal of the entire lung on either side). Both wedge resections and segmentectomies (which may also be referred to as a sub-lobar resection) are less invasive than more extensive lung surgeries such as lobectomies or pneumonectomies and may preserve more lung functions.

During such a surgery, the lung to be operated on may be collapsed (partially or entirely) because the air may be exhausted out. This can yield more space in the chest cavity for the surgery and make it easier to manipulate surgical instruments. However, this may introduce discrepancies between a 3D model and the reality during the surgery because the CT/MRI scans and X-ray images based on which the patient's 3D model is established are obtained in the presence of respiratory activities of the patient. That is, the 3D model is established based on images acquired when the patient's lungs are in their regular physiological status, i.e. filled with air. Such discrepancies can be in both appearance and dimensions between the deflated lung during the surgery and non-delated lung rendered in the 3D model. In this situation, a surgeon has to, during the surgery, overcome the obstacles created by of such discrepancies based on a mental mapping between the two based on experience in order to decide where to cut, how wide and deep the cut should be, etc. This will lead to inconsistency in surgical performance and unpredictability.

Thus, there is a need for methods and systems that address the deficiency of existing approaches to provide more realistic preoperative planning with improved precision and enhanced safety.

SUMMARY

The teachings disclosed herein relate to methods, systems, and programming for preoperative planning. More particularly, the present teaching relates to methods, systems, and programming related to preoperative planning.

In one example, a method for preoperative planning is disclosed, which is implemented on a machine having at least one processor, storage, and a communication platform capable of connecting to a network. Input data acquired with respect to a part of a patient is received. The part corresponds to an organ of the patient to be operated on and includes one or more lesions to be removed during the operation. Then, an anatomic 3D model of the part of the patient is generated. Based on the generated anatomic 3D model, a preoperative plan for linear-cutting stapler resection of the one or more lesions from the organ to be carried out during the operation is obtained. A stapler cartridge size and staple length are estimated based on the preoperative plan. Further, the resection based on the preoperative plan is visualized.

In a different example, a system for preoperative planning is disclosed. The system comprises an input data receiving unit, an anatomic 3D model generating unit, a plan obtaining unit and a plan visualizing unit. The input data receiving unit receives input data acquired with respect to a part of a patient. The part corresponds to an organ of the patient to be operated on and includes one or more lesions to be removed during the operation. The anatomic 3D model generating unit generates an anatomic 3D model of the part. The plan obtaining unit obtains a preoperative plan for linear-cutting stapler resection of the one or more lesions from the organ to be carried out during the operation based on the generated anatomic 3D model. The plan visualizing unit estimates stapler cartridge size and staple length based on the preoperative plan. The plan visualizing unit also visualizes the resection based on the obtained preoperative plan.

Other concepts relate to software for implementing the present teaching. A software product, in accord with this concept, includes at least one machine-readable non-transitory medium and information carried by the medium. The information carried by the medium may be executable program code data, parameters in association with the executable program code, and/or information related to a user, a request, content, or other additional information.

In one example, a machine-readable, non-transitory and tangible medium is disclosed, which has data recorded thereon for preoperative planning. The medium, when read by the machine, causes the machine to perform a series of steps. Input data acquired with respect to a part of a patient is received. The part corresponds to an organ of the patient to be operated on and includes one or more lesions to be removed during the operation. An anatomic 3D model of the part of the patient is generated. Based on the generated anatomic 3D model, a preoperative plan for linear-cutting stapler resection of the one or more lesions from the organ to be carried out during the operation is obtained. The stapler cartridge size and the staple length are estimated based on the preoperative plan. The resection based on the preoperative plan is visualized.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The methods, systems and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to facilitate a thorough understanding of the relevant teachings. However, it should be apparent to those skilled in the art that the present teachings may be practiced without such details. In other instances, well known methods, procedures, components, and/or software/hardware/firmware have been described at a relatively high-level, without detail, in order to avoid unnecessarily obscuring aspects of the present teachings.

The present teaching aims to address the deficiencies of the traditional approaches in preoperative planning. In the solution disclosed herein, to plan surgical resection of a lesion, the shape, size, orientation and/or position of the resection can be determined via image recognition and big data. In addition, the planned characteristics of the resection can be utilized efficiently to estimate relevant parameters of the surgical instruments to be used in the operation. Further, the planning results can be visually rendered to the user in a realistic and intuitionistic manner. Although the description provided herein is directed to planning a wedge resection with a linear cutting stapler in Video Assisted Thoracic Surgery, the present teaching is not limited to the application specifically disclosed. The present teaching is applicable to open surgery on other organs and/or with other surgical instruments.

It is commonly known that the resection of a lesion in VATS is usually based on local approaches, such as a wedge-shaped resection or lung segmentectomy. In the wedge-shaped resection, only a portion of the lung containing the lesion is removed. The lung segmentectomy is a procedure where the segment containing the lesion is removed without affecting other lung segments to preserve maximum lung functions.

Figure 1:
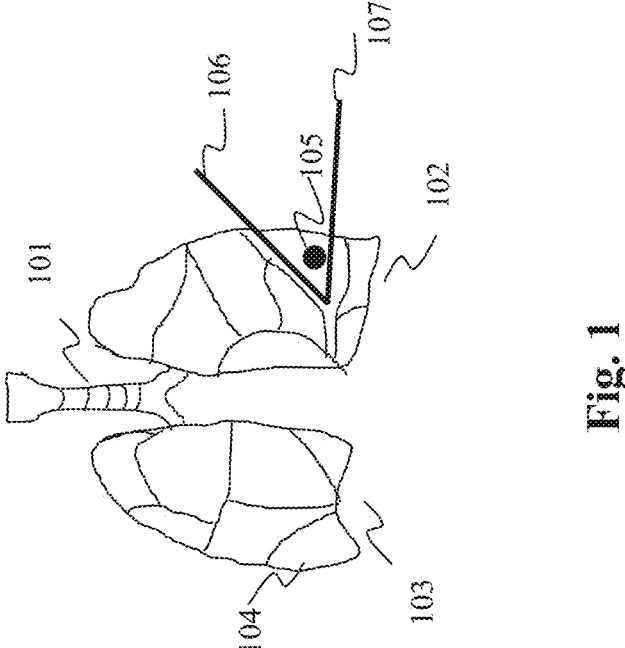
FIG. 1 schematically illustrates the anatomy of lung segments and a wedge resection performed on one of the lung segments.

FIG. 1 schematically illustrates the anatomy of lung segments and a wedge resection performed on one of the lung segments. In FIG. 1, the reference number 101 represents the trachea, 102 the left lung, and 103 the right lung. Each lung (left and right) is known to be divided into a number of lung segments. Every one of such segments is supplied by its associated bronchus for airflow. Each bronchopulmonary segment is separated from the rest of the lung by a septum of connective tissue. This property allows a lung segment to be surgically operated on without affecting other segments. The regions 104 inside the lungs 102-103 are illustration of a plurality of lung segments. A lesion is indicated by 105. Two resection lines 106 and 107 represent a wedge resection on one of the lung segments 104. Although it is shown that the cutting starts from the side of the lung, this is not always necessary. Depending on the location of the lesion, the lung may be manipulated to fold in the middle to perform a resection. For example, cutting may start in the direction substantially perpendicular to the surface of the paper of FIG. 1 as well.

Figure 2:
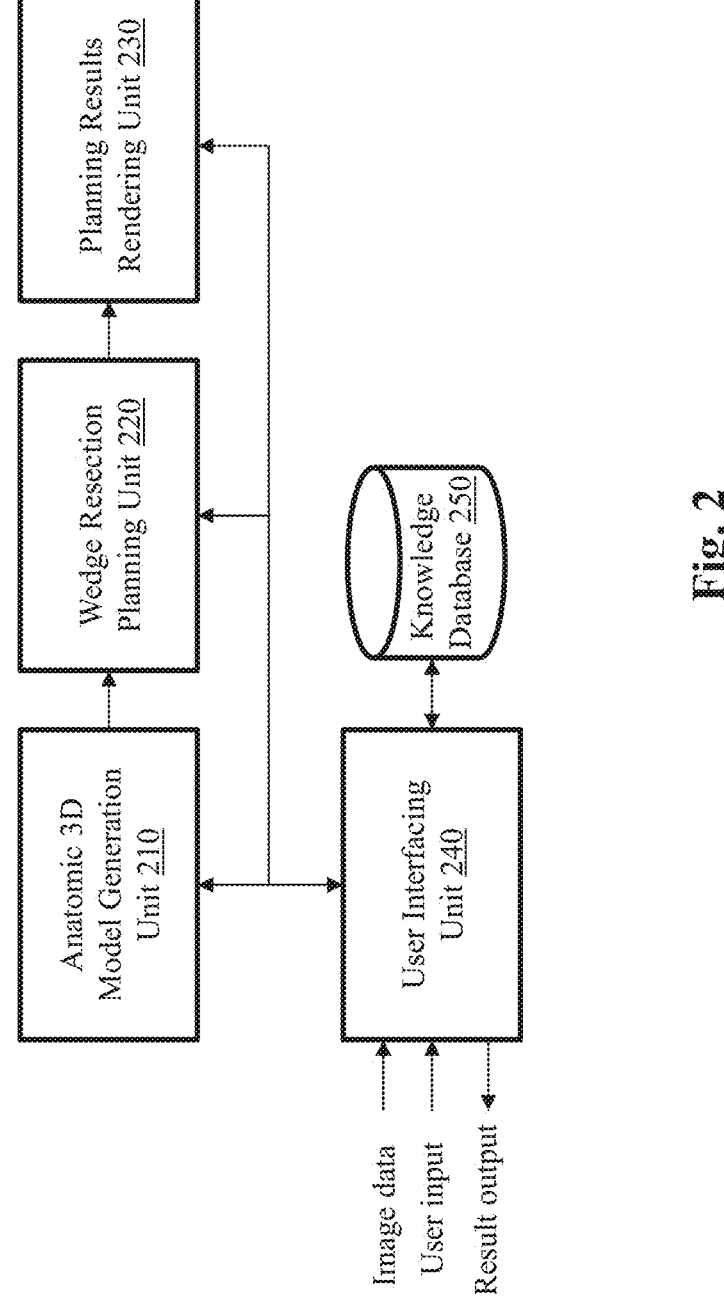
FIG. 2 depicts an exemplary high level system diagram of an overall system for surgical resection planning, in accordance with an exemplary embodiment of the present teaching.

FIG. 2 depicts an exemplary high level system diagram of an overall system for surgical resection planning, in accordance with an exemplary embodiment of the present teaching. The overall system comprises an anatomic 3D model generation unit 210, a wedge resection planning unit 220, a planning results rendering unit 230, a user interfacing unit 240 and a knowledge database 250. The knowledge database 250 is provided to store the information that will be used in the generation of the 3D model. Such information may be loaded from cloud during the initialization process of the system. It may be dynamically updated via machine learning and big data management.

Figure 3:
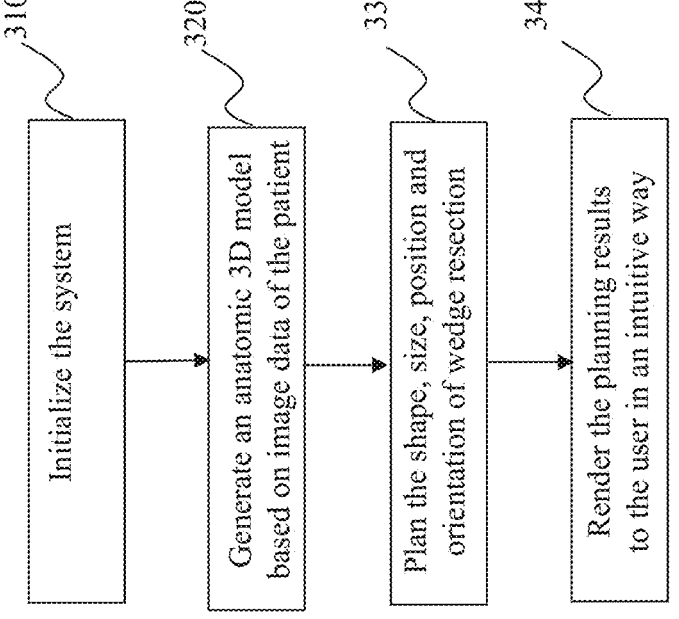
FIG. 3 is a flowchart of exemplary processes of an overall system for surgical resection planning, in accordance with exemplary embodiments of the present teaching.

FIG. 3 is a flowchart of exemplary processes of the overall system for surgical resection planning, in accordance with exemplary embodiments of the present teaching. The process 300 is initialized at 301 by receiving the image data of the patient via the user interface unit 240. During the initialization, relevant knowledge or information such as models for recognizing various anatomies, criteria for the planning to meet, and specifications of surgical instruments to selected, may be loaded to facilitate the following processes. Inputs may be received via the user interface unit 240 for the purposes of controlling or fine-tuning in the processes.

Subsequently, at 320, the anatomic 3D model generation unit 210 may build an individualized or personalized anatomic 3D model for the patient based on his or her image data, in accordance with the loaded knowledge. Based on the 3D anatomic model built by the anatomic 3D model generation unit 210, at 330, the wedge resection planning unit 220 may plan a wedge resection in terms of various characteristics (such as shape, size, orientation and position), in accordance with the inputs from the user. Further, at 340, the planning results rendering unit 230 may calculate or estimate certain parameters of surgical instruments (such as a linear cutting stapler) based on the relevant characteristics of the planned resection, and render the results in a vivid and intuitive way. During the process, not merely the (final) results, optionally, certain intermediate results, such as the generated 3D model, the planned wedge shape, etc., may be rendered to the user via the user interface unit 240 as well.

The specific functions and operations of the modules and processes shown in FIGS. 2-3 will be explained with more details in the following.

Figure 4:
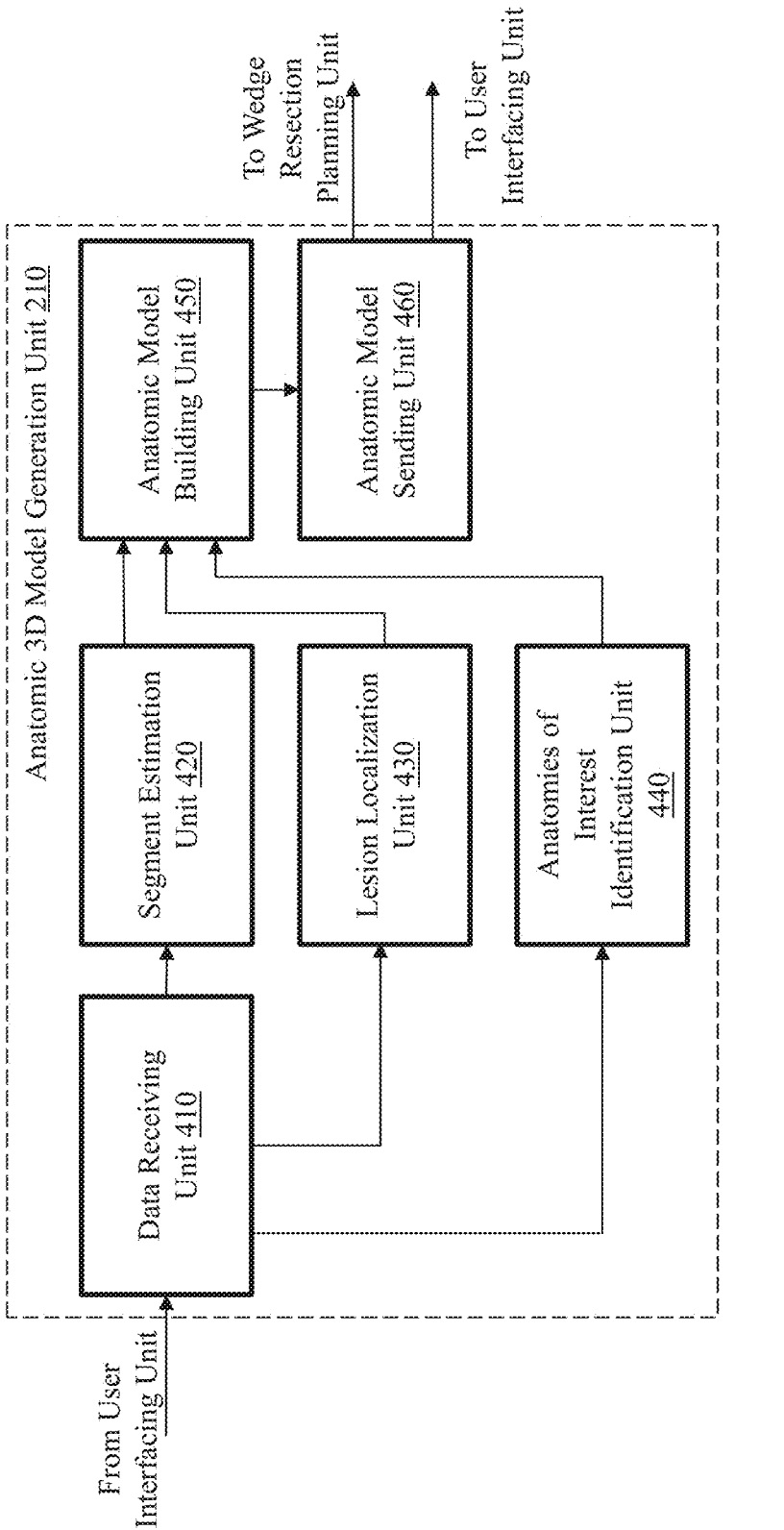
FIG. 4 depicts an exemplary high level system diagram of an anatomic 3D model generation unit, in accordance with an exemplary embodiment of the present teaching.

FIG. 4 depicts an exemplary high level system diagram of the anatomic 3D model generation unit 201 as shown in FIG. 2, in accordance with an exemplary embodiment of the present teaching. In operation, since each individual patient's lung physiology is different, to obtain a personalized model of lung segments, a CT/MRI scan of the patient may be inputted. Based on the inputted image data, a 3D model of the bronchus may be built, from which the lung segments may be divided, and other anatomies, such as lesions, pulmonary arteries, pulmonary veins may be identified. As illustrated in FIG. 4, the anatomic 3D model generation unit 201 comprises a data receiving unit 410, a segment estimation unit 420, a lesion localization unit 430, an anatomies of interest identification unit 440, an anatomic model building unit 450 and an anatomic model sending unit 460.

Figure 5:
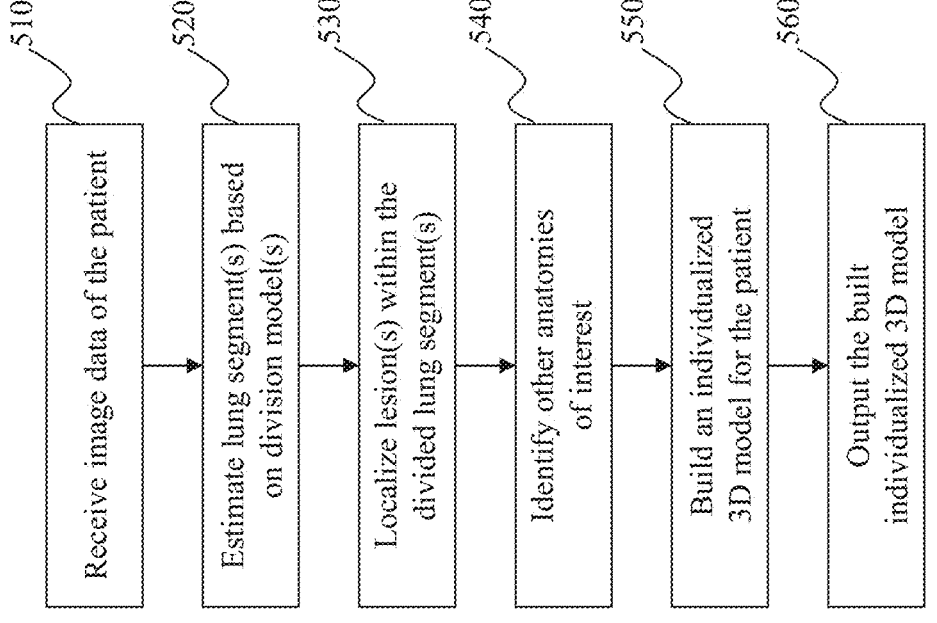
FIG. 5 is a flowchart of exemplary processes of an anatomic 3D model generation unit, in accordance with exemplary embodiments of the present teaching.

FIG. 5 is a flowchart of exemplary processes of the anatomic 3D model generation unit 201, in accordance with exemplary embodiments of the present teaching. First, the process 500 starts at 510 with receiving image data of the patient and certain inputs from the user by the data receiving unit 410. Then, the data receiving unit 410 may forward the relevant data to different units 420-440.

Based on the data received from the data receiving unit 410, at 520, the segment estimation unit 420 may estimate the segments of the lung. Estimation of the lung segments may be carried out automatically or semi-automatically based on division models retrieved from the knowledge database 250. In one embodiment, lung segments may be divided by means of recognizing different bronchus brunches, as each bronchus branch corresponds to one lung segment. More specifically, initially, bronchus branches may be automatically or manually labeled based on medical knowledge, for example. Then, with respect to each pixel inside the lung, the pixel may be assigned to the corresponding segment if it is closest to bronchus branch representing the segment. In one embodiment, lung segments may need to be estimated only with respect to the bronchial branches close to the lesion to be resected. In another embodiment, all lung segments may be estimated.

Subsequently, the lesion localization unit 430 may localize the lesions within the divided lung segments at 530, and other anatomies of interest may also be identified by the anatomies of interest identification unit 440 at 540, from the image data of the patient. The localization of the lesions may be achieved based on the lesion models retrieved from the knowledge databases 250. The anatomies of interest may include, but not limited to, 3D lung, bronchus, lesions, pulmonary arteries, and pulmonary veins, etc.

Based on the results from the segment estimation unit 420, the lesion localization unit 430 and the anatomies of interest identification unit 440, at 550, the 3D model building unit 450 may create a 3D anatomic model of the lung of the patient. Via the anatomic model sending unit 460, the 3D model as generated by the 3D model building unit 450 is sent out at 560 for subsequent processing. Optionally, the generated 3D model is also sent for rendering via the user interfacing unit 240 on a display (not shown in the figures).

In the below, the principal of planning wedge resection is to be explained with reference to FIGS. 6A-7C, in accordance with an exemplary embodiment of the present teaching.

Figure 6B:
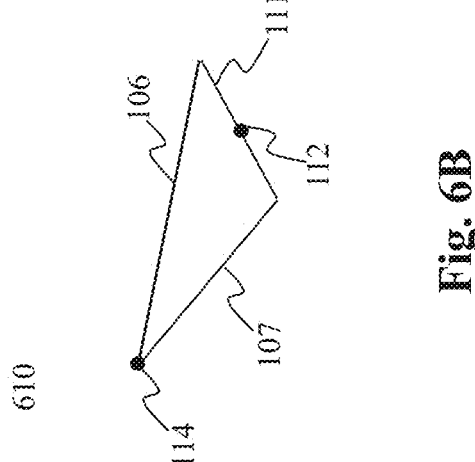
FIG. 6B shows a simplified conceptual exemplary schematic for the wedge resection.
Figure 6A:
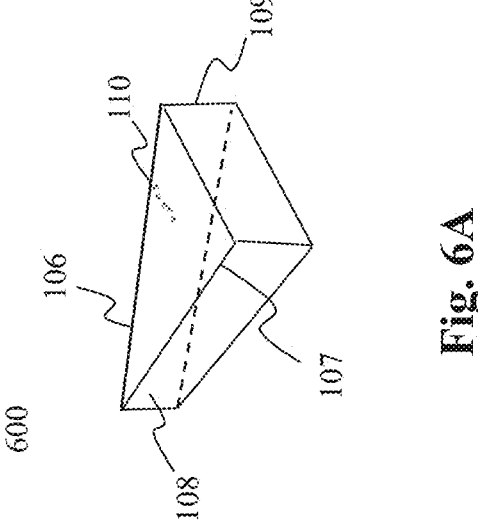
FIG. 6A shows a conceptual exemplary schematic for a wedge resection as an instance of surgical resections.

FIG. 6A shows a conceptual exemplary schematic for a wedge resection performed on the lung surface. In the side view of the wedge shape 600 shown in FIG. 6A, reference numbers 108 and 110 represent surfaces formed along cutting lines 106 and 107 of a surgical instrument such as a linear cutting stapler and may be called cutting surfaces. The height 109 of the wedge shape 600 represents the thickness of the lung after folding.

FIG. 6B shows a simplified conceptual exemplary schematic for the wedge resection. Compared with FIG. 6A, the height or thickness 109 of the wedge is ignored in the wedge shape 610 shown in FIG. 6B. This is reasonable, since the top and bottom surfaces of the lung will be collapsed together in the local region of cutting. For example, with the operation of a linear cutting stapler, they will be cut and firmly pressed to have a thickness between 2 mm to 4 mm, which is in the range of the typical staple length of a linear cutting stapler on the market.

As shown in FIG. 6B, two cutting lines 106 and 107 together with a base line 111 of the simplified wedge shape 610 define a triangular profile. The tip-vertex of the triangular profile is represented by reference number 114, and 112 indicates the center point of the base line 111. The main goal of resection planning is to determine the profile, position and orientation of the simplified wedge shape 610 on the surface of lung with respect to the lung segments, the lesion, and other critical anatomic structures that may need to be avoided during the resection.

Figure 7B:
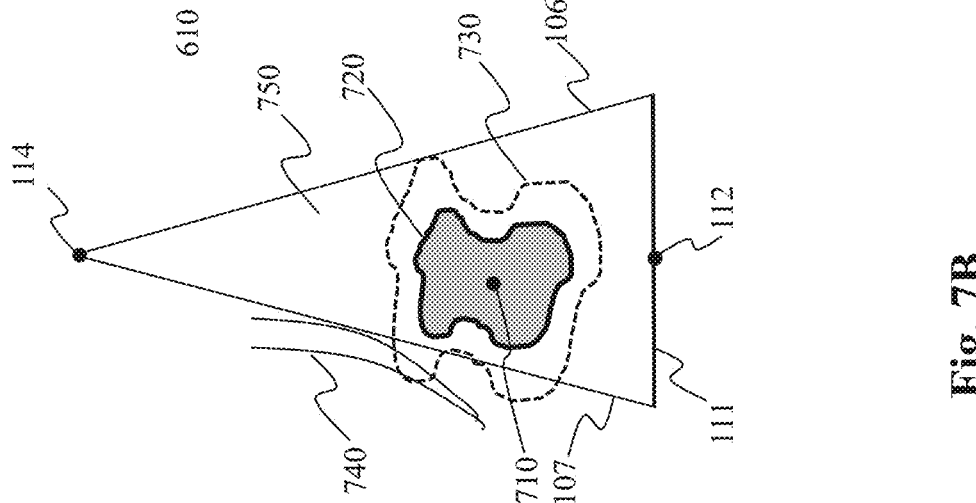
FIGS. 7A-7B depict different exemplary planning options of a wedge resection in which a lesion, a safety margin, and other anatomical structure(s) of interest are projected onto a basis plane of wedge resection, in accordance with embodiments of the present teaching.
Figure 7A:
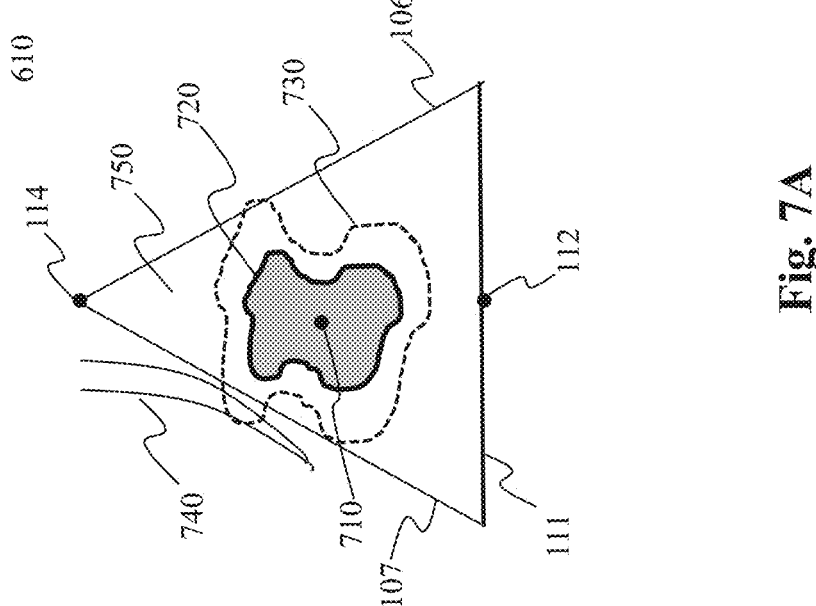

FIG. 7A depicts an exemplary planning option of wedge resection, in accordance with embodiments of the present teaching. In FIG. 7A, an example of the collapsed anatomic objects is exemplarily illustrated. That is, certain objects are collapsed onto the basis plane 750 defined by the center 710 of the lesion and the base line 111. The reference number 720 represents the collapsed boundary of the lesion, 730 represents the collapsed 3D safety margin boundary, 740 represents a vascular structure near the lesion.

FIG. 7B illustrates another exemplary planning option of the length of the base line and the position of the vertex-tip, in accordance with embodiments of the present teaching. Compared with the determination shown in FIG. 7A, in FIG. 7B, the length of the base line 111 is shorter. With the new length, the cutting line 107 may be automatically generated by avoiding the nearby vessel 740. Another cutting line 106 may also be automatically determined by find a line tangent to the boundary of the safety margin 730. Then, the intersection of the cutting lines 106 and 107 may determine the position of the tip-vertex 114.

To decide which options shown in FIGS. 7A and 7B is a better resection plan, different criteria may be applied. One example of the criteria may be to find a resection plan which leads to a minimum area of the base plane (that is, to determine which one of the two triangles 106-111-107 in FIG. 7A—7B has a smaller area). This is reasonable, since resection usually strives to remove as less healthy tissues as possible. Another exemplary criterion may be a combination of the area of the base plane and other considerations, such as degree of inflammation along the cutting lines 106-107. For example, a weighted average of the area and degree of inflammation may be calculated and used as an error measure. The purpose is then to find a resection plan that yields the minimum error measure.

Figure 7D:
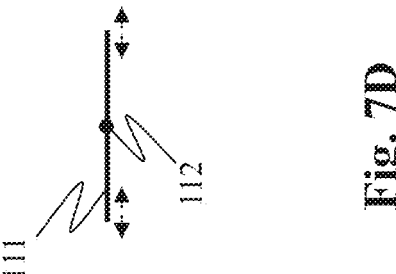
FIGS. 7C-7D depict exemplary adjustment of the orientation and length of a base line for wedge resection, in accordance with embodiments of the present teaching.
Figure 7C:
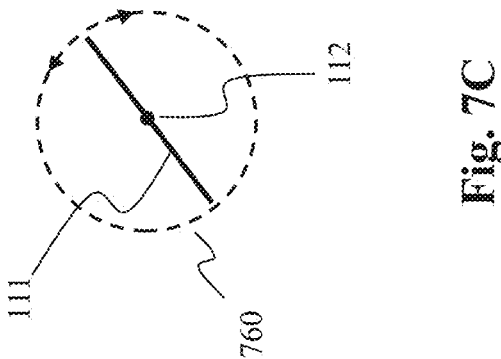

FIGS. 7C-7D depict exemplary manual adjustment of the orientation and length of the base line 111 for wedge resection, in accordance with embodiments of the present teaching. In the illustrated example of FIG. 7C, the adjustment may be carried out through a dial-like adjuster provided via the user interfacing unit 240. By grabbing and dragging the base line 111 to any desirable angle, the user may rotate the base line 111 around the center point 112 to select orientation based on ease of operation and other medical considerations. The reference number 760 represents the rotation trajectory of the base line 111 during orientation selection. Similarly, by dragging on a sliding bar which may be provided on the user interfacing unit 240, selection of the length of the base line 111 may be carried out by adjusting the position of either or both end points of the base line 111.

Figure 8:
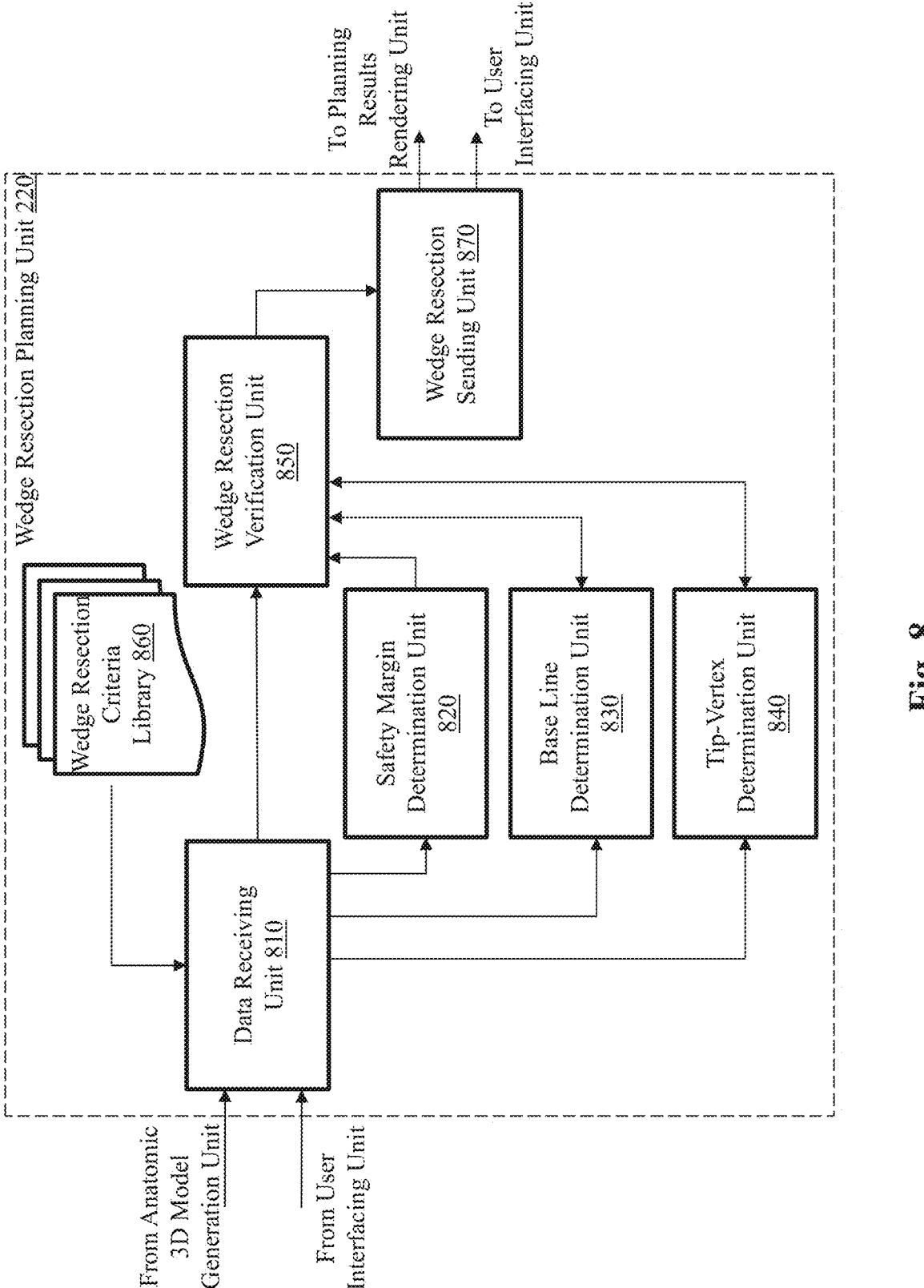
FIG. 8 depicts an exemplary high level system diagram of a wedge resection planning unit, in accordance with an exemplary embodiment of the present teaching.

FIG. 8 depicts an exemplary high level system diagram of the wedge resection planning unit 220, in accordance with an exemplary embodiment of the present teaching. As illustrated in FIG. 8, the wedge resection planning unit 220 comprises a data receiving unit 810, a safety margin determination unit 820, a base line determination unit 830, a tip-vertex determination unit 840, a wedge resection verification unit 850, a wedge resection criteria library 860 and a wedge resection sending unit 870. Although the wedge resection criteria library 860 is illustrated as a separate component comprised in the wedge resection planning unit 220, it may be incorporated in the knowledge database 250 shown in FIG. 2.

Figure 9:
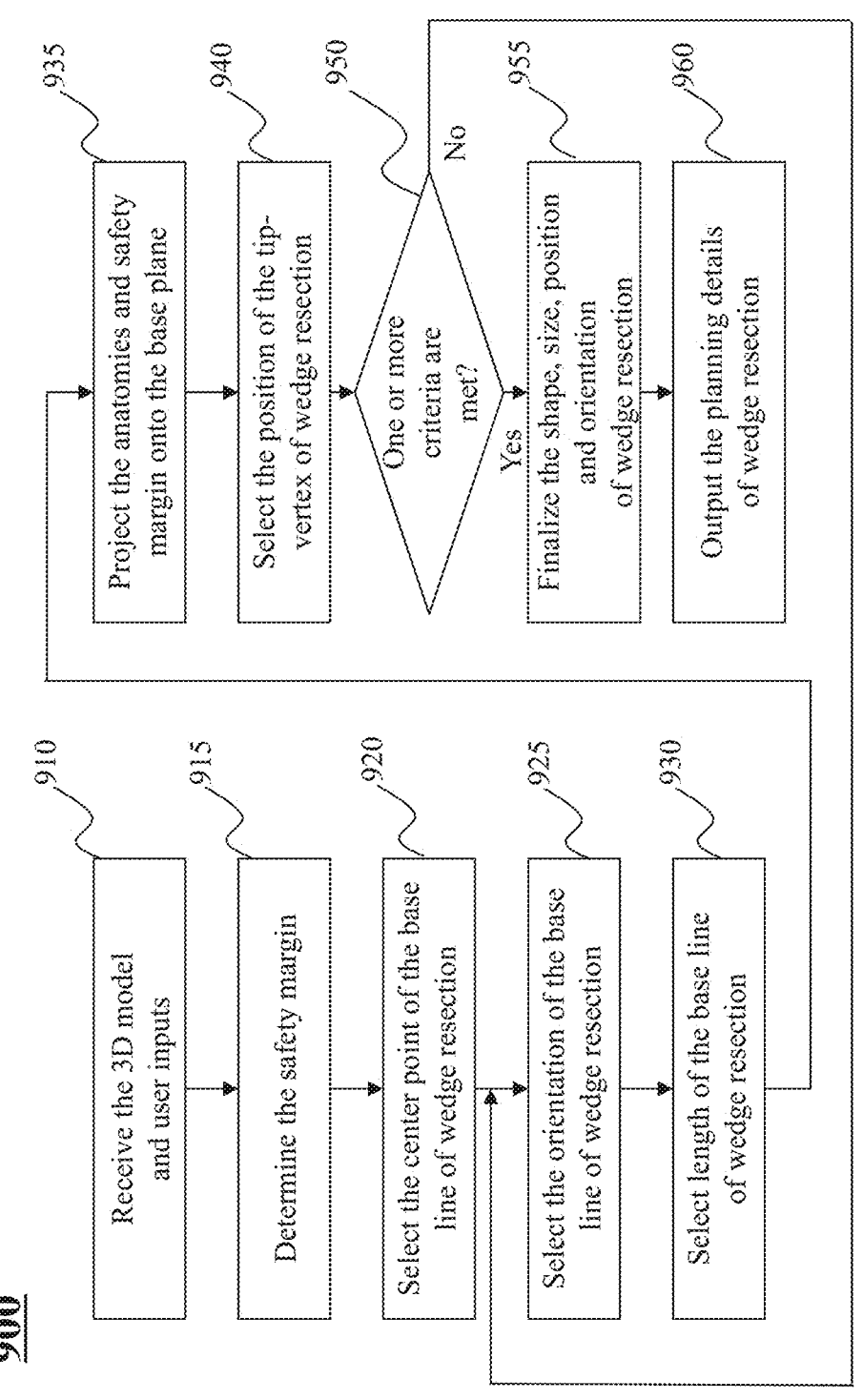
FIG. 9 is a flowchart of exemplary processes of a wedge resection planning unit, in accordance with exemplary embodiments of the present teaching.

FIG. 9 is a flowchart of exemplary processes of the wedge resection planning unit 220, in accordance with exemplary embodiments of the present teaching. The process 900 starts at 910 in which the data receiving unit 810 may receive the personalized 3D model of the patient from the anatomic 3D model generation unit 210 and user inputs from the user interfacing unit 240, and forward the relevant signals to corresponding components.

Then, at 915, based on the data received from the data receiving unit 810, the safety margin determination unit 820 may determine the safety margin which is to be used in the planning of the wedge resection. As can been see from FIGS. 7A-7B, the safety margin determines the extra tissue to be cut surround the lesion. In an embodiment, a 3D safety margin may be obtained by the safety margin generation unit 820 based on a lesion model (retrieved from, for example, the knowledge database 250). In another embodiment, a 3D safety margin may be obtained in accordance with margin value defined by the user (for example, received from the user via the user interface unit 240). Upon receiving such a value, the safety margin generation unit 820 may generate a 3D safety margin surface by defining an iso-distance surface from the lesion surface, with the distance being the margin value. Further, the generated 3D safety margin surface may be locally re-defined by the user, e.g., to avoid a major vessel.

Based on the data sent from the data receiving unit 810, at 920-930, the base line determination unit 830 may determine various parameters pertaining to the base line 111 of the wedge resection, including the position of the center point 112 on the lung surface, and the length and orientation of the base line 111. First of all, at 920, a point on the lung surface may be selected as the center point 112 of the base line 111. In an embodiment, the center point 112 may be automatically determined as the point of shortest distance to the center 710 or the surface 720 of the lesion (as shown in FIG. 7A—7B). In another embodiment, the center point 112 may be manually positioned by the user onto any desirable point on the lung surface of the involved lung segment.

Then, the process 900 proceeds to select the orientation and the length of the base line 111 at 920 and 925. In an embodiment, the selection of the orientation and length of the base line 111 may be carried out in the manner shown in FIGS. 7C-7D. Alternatively, the length of the base line 111 may be automatically selected by means of the method described in connection with FIGS. 7A-7B.

Once the basis line 111 is determined, at 935, the tip-vertex determination unit 840 may project the safety margin surface determined at 915 and the lesion and other critical anatomies of interest in the lung segment onto the basis plane 750 defined by the center 710 of the lesion and the base line 111. Then, at 940, the tip-vertex determination unit 840 may select the tip-vertex 114 of the wedge shape on the basis plane 750. In one embodiment, the tip-vertex 114 may be manually positioned by the user onto any desirable point on the basis plane 750. In another embodiment, the position of the tip-vertex together with the length of the base line 111 may be automatically determined by cooperation of the base line determination unit 830 and the tip-vertex determination unit 840 based on applicable criteria, in accordance with the principal illustrated in FIGS. 7A-7B.

After the base line 111 and the tip-vertex 114 are determined, two cutting lines 106 and 107 may be drawn by connecting the tip-vertex 114 and the two end points of the base line 111. The cutting lines 106-107 together with the base line 111 determine what is to be cut in the resection. Then, the process 900 may proceed to 950, where the wedge resection verification unit 850 may verify whether the resection meets certain pre-determined criteria retrieved from the wedge resection criteria library 860. If the applied criteria are not met at 955, the process 900 may loop back to 925, such that the orientation and/or length of the base line 111 and/or the position of the tip-vertex 114 may be redetermined or re-selected. Instead, if the resection plan is verified as acceptable based on the applied criteria, the details about the shape, size, position and orientation of the resection are determined and/or finalized at 955 and then outputted at 960 by the wedge resection sending unit 870, for display and/or further processing. Although FIG. 9 shows that the re-selection is achieved by looping back to 925, in alternative examples, the process 900 may go back to 915, 920, 930, 935 or 940 to re-determinate the corresponding parameters accordingly.

Applicable criteria may include, but not limited to, whether the resection 610 is confined within the associated single lung segment 104, whether the collapsed safety margin boundary (exemplified as 730 in FIG. 7A—7B) can be covered, and whether some critical vascular structure (exemplified as 740 in FIG. 7A—7B) can be avoided, etc. Also, applicable criteria may be based on other different medical considerations, including but not limited to, whether the areas close to the cutting lines 106 and 107 are free of inflammation, whether the tissue thickness on both sides of the cutting lines allow a stable stapling, or the like.

In an embodiment, the inflammation status may be visually inspected. In another embodiment, the inflammation status may be automatically determined based on density of the lung tissue in the image data (such as CT images). For example, in the situation that a linear cutting stapler is to be used to close the enterotomy created by the surgeon, there are usually 2 to 3 rows of staples on each side of the cutting line, which makes about a 1-2 cm width for the staple cartridge. Within a band of this width, the mean density of the lung tissue in the CT images may be computed along the cutting lines 106-107. An empirical average value may be obtained from normal, non-inflamed tissue. When an average value is above this empirical value, the tissue may be determined as being inflamed. Instead of using average value, as alternative, the maximum value may be used for the same purpose. It is noted that vascular structures may need to be subtracted during such computation. To determine whether the tissue thickness on both sides of the cutting line may warrant a stable stapling, for example, the tissue thickness before clamping by the stapler may be used to facilitate the estimation. More details with respect to this example will be further provided below in connection with FIG. 13A.

Figure 10A:
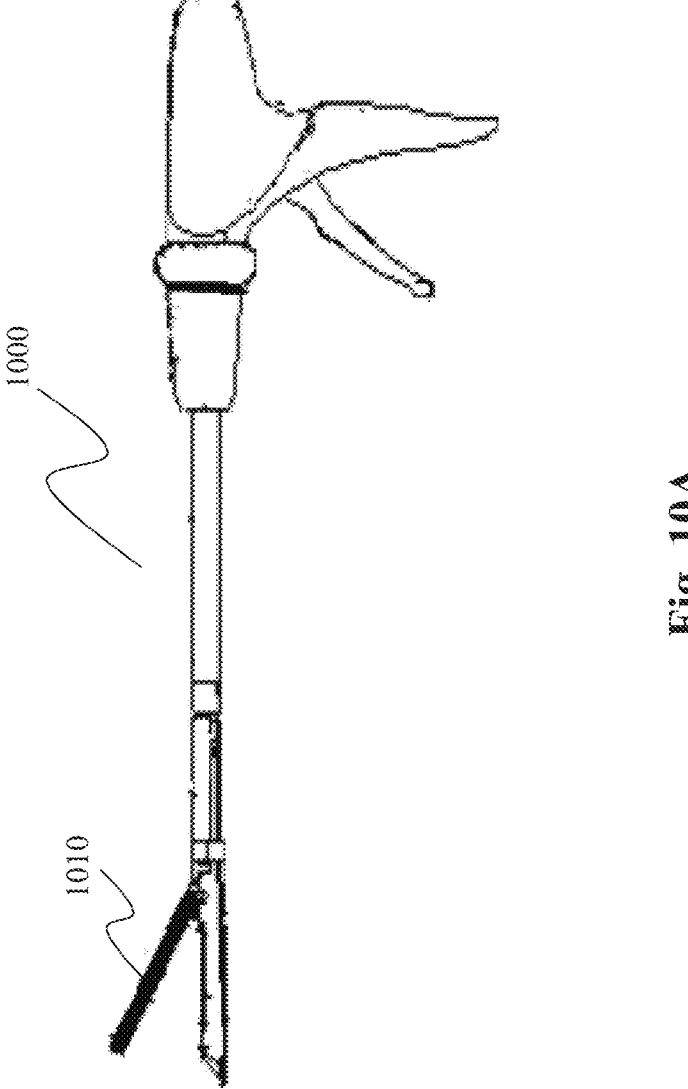
FIGS. 10A-C depict an exemplary linear cutting stapler, an exemplary staple cartridge, and an exemplary staple that may be used to perform a wedge resection as planned in accordance with exemplary embodiments of the present teaching.
Figure 10C:
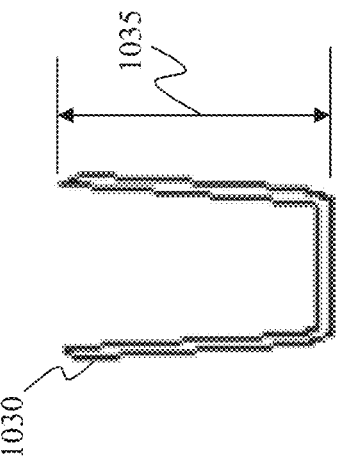
Figure 10B:
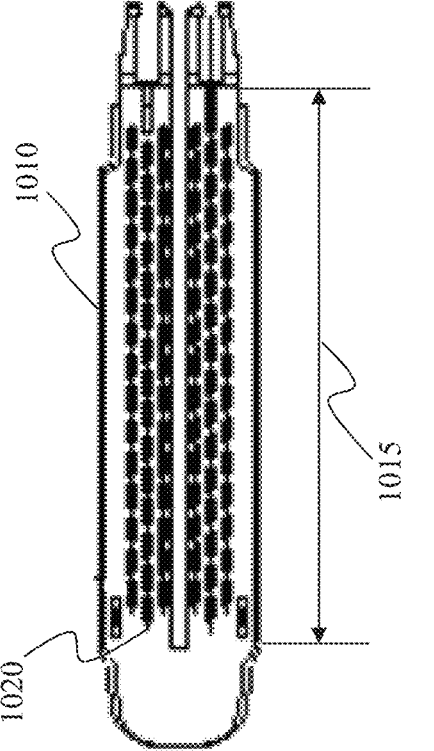

A variety of surgical tools may be used for surgical resection, including but not limited to electric scalpels, ultrasonic scalpels, and linear cutting staplers. FIGS. 10A-10C depict an exemplary linear cutting stapler, an exemplary staple cartridge, and an exemplary staple that may be used to perform a wedge resection as planned in accordance with exemplary embodiments of the present teaching. Typically, a linear cutting stapler may be used in abdominal surgery, thoracic surgery, gynecology and pediatric surgery, performing both cutting and stitching at the same operation. In FIG. 10A, the linear cutting stapler 1000 may be loaded with replaceable staple cartridges 1010 of different lengths. FIG. 10B illustrates with more details the staple cartridges 1010, in which rows 1020 of staples may be loaded. FIG. 10C shows a side view of a staple 1030. The reference number 1015 represents the length of the staple cartridge 1010, and 1035 represents the length of the staple 1030.

To provide enhanced experience, in the preoperative planning scheme disclosed in the present teaching, rendering of planning results may include not only to display the position of the lesion, the safety margin around the lesion and critical anatomical structures to be avoided in the 3D model of the patient, but also to inform the user of the position of the cutting lines, the length of the staple cartridge(s) to be selected, and the length of the staple(s) to be selected. In an example, the cartridge length is estimated based on the length of the cutting line. As another example, the staple length may be estimated based on the thickness of the tissues to be stapled.

In the following, referring to FIGS. 11-13B, improved rendering of the planning results is explained in accordance with exemplary embodiments of the present teaching.

Figure 11:
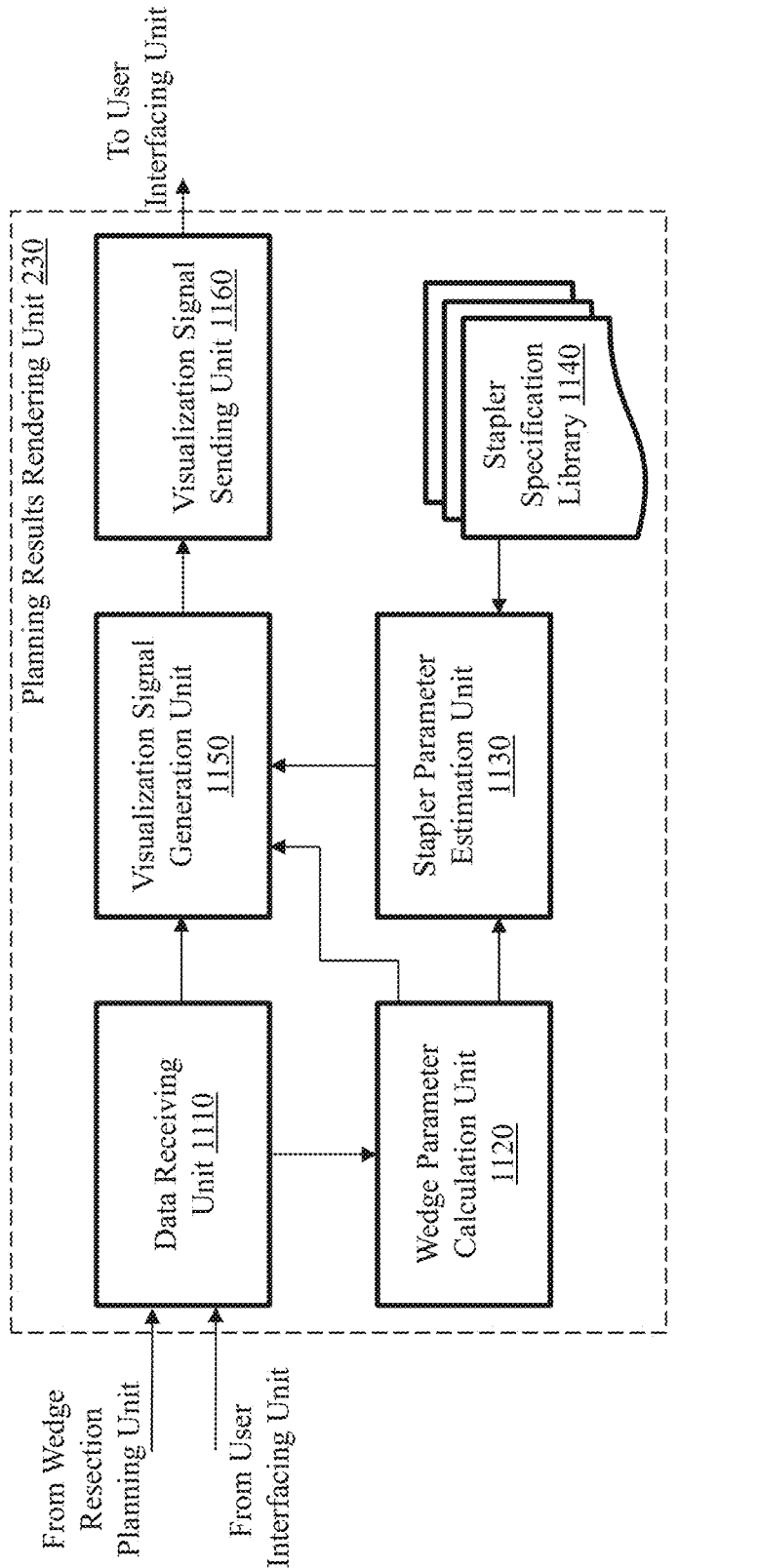
FIG. 11 depicts an exemplary high level system diagram of a resection planning result rendering unit, in accordance with an exemplary embodiment of the present teaching.

FIG. 11 depicts an exemplary high level system diagram of the planning results rendering unit 230, in accordance with an exemplary embodiment of the present teaching. As shown in FIG. 11, the planning results rendering unit 230 comprises a data receiving unit 1110, a wedge parameter calculation unit 1120, a stapler parameter estimation unit 1130, a stapler specification library 1140, a visualization signal generation unit 1150, and a visualization signal sending unit 1160. Although the stapler specification library 1140 is shown in FIG. 11 as a separate component of the planning results rendering unit 230, it may be provided in combination with the wedge resection criteria library 860 (referring to FIG. 8) which is comprised in the wedge resection planning unit 220. Alternatively, either or both of the wedge resection criteria library 860 and the stapler specification library 1140 may be incorporated in the knowledge database 250.

Figure 12:
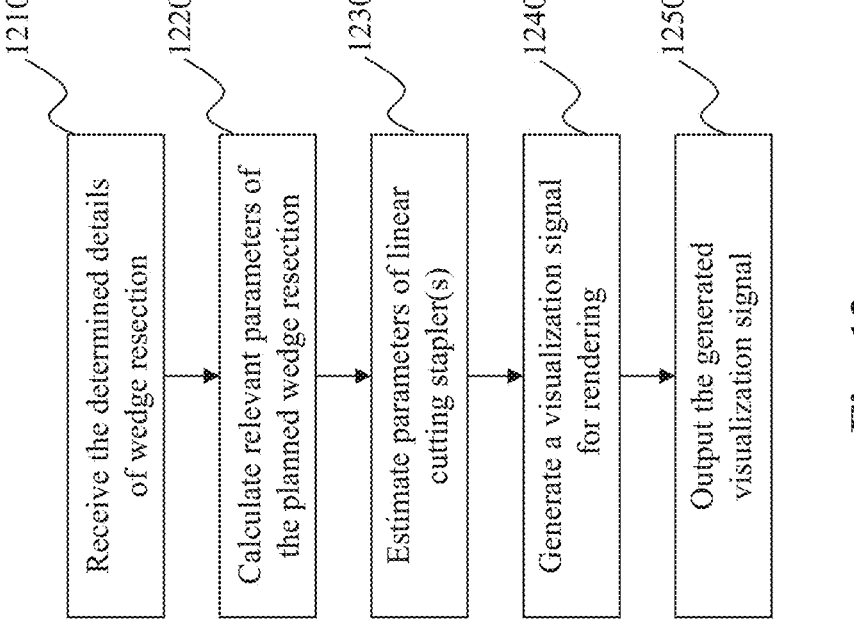
FIG. 12 is a flowchart of exemplary processes of a resection planning result rendering unit, in accordance with exemplary embodiments of the present teaching.

FIG. 12 is a flowchart of exemplary processes of the planning results rendering unit 230, in accordance with exemplary embodiments of the present teaching. The process 1200 starts at 1210 where the data receiving unit 1110 receives the planning results from the wedge resection planning unit 220 and user inputs from the user interfacing unit 240, and forwards the relevant data to the corresponding components of the planning results rendering unit 230.

Subsequently, at 1220, based on the details of the wedge resection as determined in the planning results rendering unit 230, the wedge parameter calculation unit 1120 calculates the relevant parameters of the planned wedge shape and sends the calculated results to the staple parameter estimation unit 1130 and the visualization signal generation unit 1150. For example, the angle between each of the cutting lines 106-107 and the base line 111 of the wedge shape may be calculated to guide surgical operation. Also, the length of the cutting lines 106 and 107 and/or the thickness of the tissues to be cut may be calculated to facilitate estimation of certain parameters of linear cutting stapler(s) to be used.

Then, the process proceeds to 1230, where the stapler parameter estimation unit 1130 may estimate the relevant parameters of the linear cutting stapler(s) that will be used in the surgery, based on the calculated results of the wedge parameter calculation unit 1120, in accordance with the specifications of the staplers retrieved from the stapler specification library 1140. Such parameters may include but not be limited to the length of the staple cartridges to be selected, the length of the staples to be selected, and the number of the staple cartridges to be used. Depending on the vendors of the staplers, staple cartridges may be of different length (e.g., a length of 30 cm, 45 cm, 60 cm, etc.). In one embodiment, the length of the cutting line 106-107 may be divided by the longest length of the staple cartridges first to determine how many of them may be needed. Then, the remainder may be used in a similar way for determining the number of shorter cartridges. As another example, the staple length may be estimated based on the thickness of the cutting plane. More detailed explanation in this aspect may be provided below in connection with FIG. 13A.

Figure 13B:
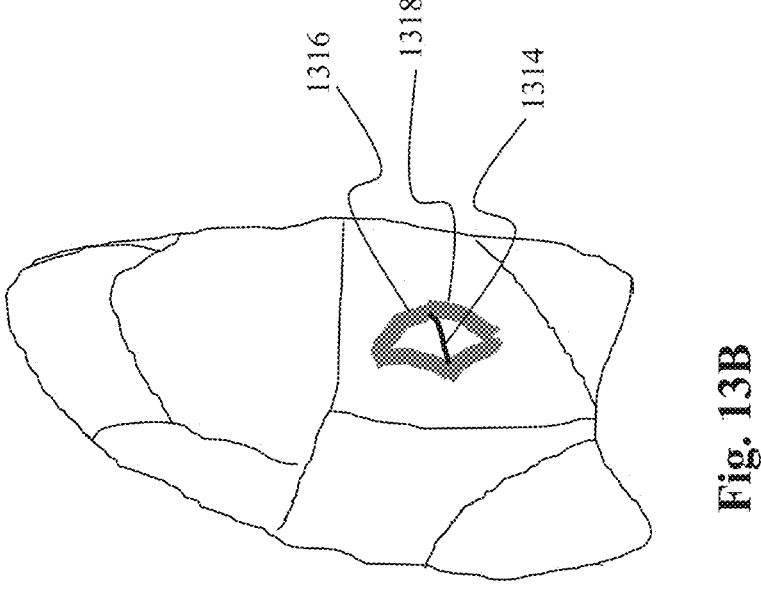
FIG. 13B shows a conceptual exemplary schematic for visualization of planned staple positions on the lung surface.
Figure 13A:
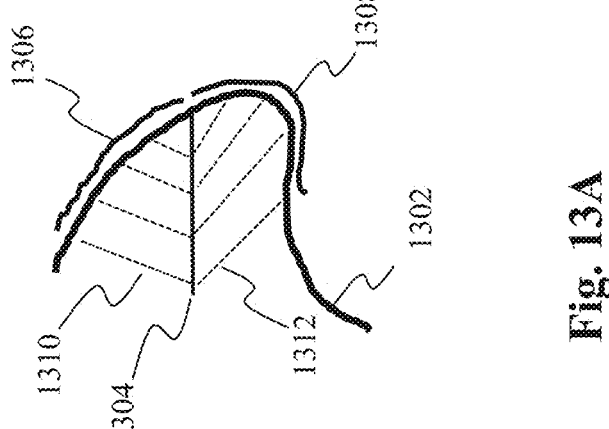
FIG. 13A shows a conceptual exemplary schematic for determination of staple cartridge length and a cutting line mapped on to the lung surface.

FIG. 13A shows a conceptual exemplary schematic for determination of staple cartridge length and a cutting line mapped on to the lung surface. In FIG. 13A, the reference number 1302 represents the lung surface before deflation (on which is the resection planning is performed), 1304 is an estimated cutting line after deflation. The dashed lines 1310 and 1312 illustrate the correspondence of points on the cutting line 1304 to the points on the lung surface 1302. The correspondence may be thought of reversing the deflation by mapping the cutting line 1304 onto the lung surface 1302. This may generate the curves 1306 and 1308 on the lung surface 1302. The length of the cutting line 1304 will be the same as the length of the curves 1306 and 1308 (length preservation during deflation). The lengths of the dashed lines 1310 and 1312 may correlate to the staple length. Since the tissues along the dashed lines may be compressed to a thickness to be stapled, the compressed thickness at each dashed line positions may be empirically estimated as a fraction of the length of the dashed lines. An alternative method to estimate the compressed thickness is to add pixel intensity in the CT image along the dashed lines. This summed intensity may be used to correlate with the compressed thickness. The brighter the summed intensity, the more tissues there are along the dashed lines, and thus thicker the compressed tissue will be. The correlation coefficient between the brightness and thickness may be estimated empirically or based on actual data collected during surgery.

FIG. 13B shows a conceptual exemplary schematic for visualization of planned staple positions on the lung surface. In FIG. 13B, the reference number 1314 represents the base line of the wedge resection, and the reference numbers 1316 and 1318 represent a ribbon of the same width as the selected staple cartridge. The shape of the ribbon may be the same as the mapped cutting lines (referring to 1306 and 1308 in FIG. 13A) on the lung surface. The ribbon may be used to represent the staple positions obtained during the wedge resection planning as disclosed in the present teaching. It is to be noted that the resection planning is performed on the model of the lung before surgery, when the lung was not deflated. Therefore, the stable position visualization is to display the staple positions on the non-deflated lung model.

Figure 14:
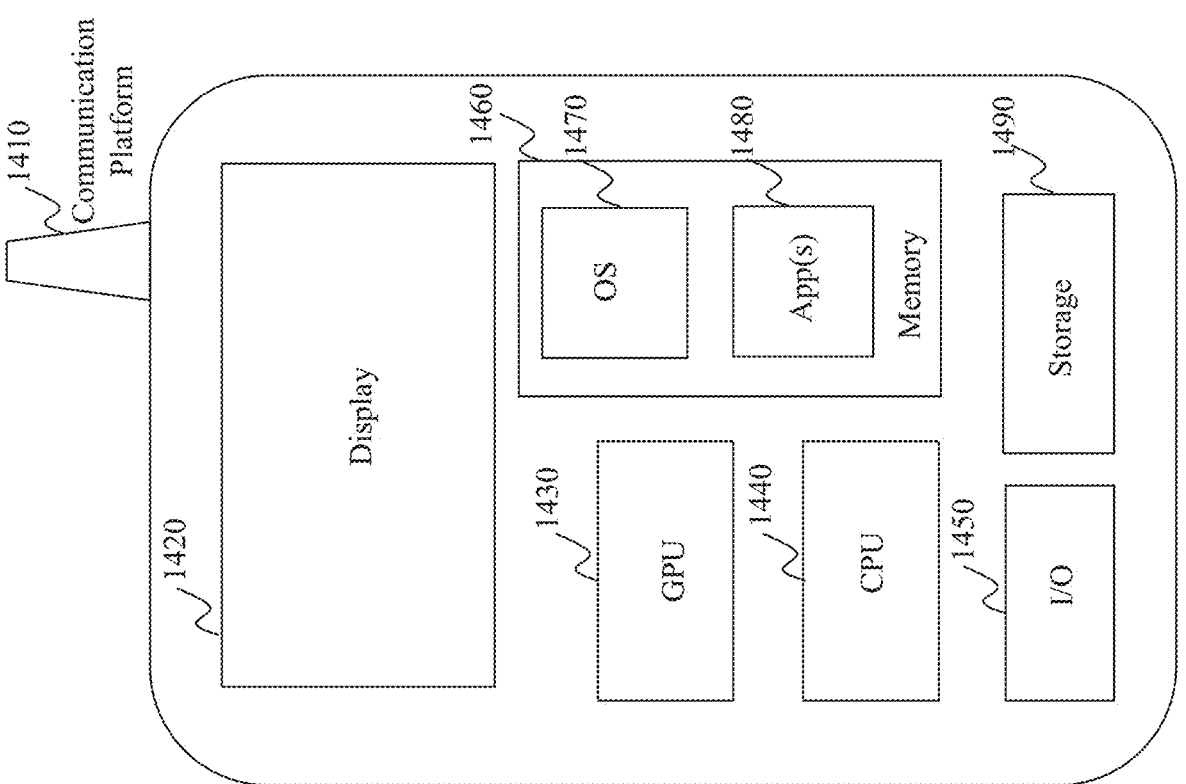
FIG. 14 is an illustrative diagram of an exemplary mobile device architecture that may be used to realize a specialized system implementing the present teaching in accordance with various embodiments.

FIG. 14 is an illustrative diagram of an exemplary mobile device architecture that may be used to realize a specialized system implementing the present teaching in accordance with various embodiments. In this example, the user device on which the present teaching may be implemented corresponds to a mobile device 1400, including, but is not limited to, a smart phone, a tablet, a music player, a handled gaming console, a global positioning system (GPS) receiver, and a wearable computing device (e.g., eyeglasses, wrist watch, etc.), or in any other form factor. Mobile device 1400 may include one or more central processing units ("CPUs") 1440, one or more graphic processing units ("GPUs") 1430, a display 1420, a memory 1460, a communication platform 1410, such as a wireless communication module, storage 1490, and one or more input/output (I/O) devices 1450. Any other suitable component, including but not limited to a system bus or a controller (not shown), may also be included in the mobile device 1400. As shown in FIG. 14, a mobile operating system 1470 (e.g., iOS, Android, Windows Phone, etc.), and one or more applications 480 may be loaded into memory 1460 from storage 1490 in order to be executed by the CPU 1440. The applications 1480 may include a browser or any other suitable mobile apps for managing a preoperative surgical planning and simulation system according to the present teaching on mobile device 1400. User interactions, if any, may be achieved via the I/O devices 1440 and provided to the various components connected via network(s).

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to appropriate settings as described herein. A computer with user interface elements may be used to implement a personal computer (PC) or other type of workstation or terminal device, although a computer may also act as a server if appropriately programmed. It is believed that those skilled in the art are familiar with the structure, programming, and general operation of such computer equipment and as a result the drawings should be self-explanatory.

Figure 15:
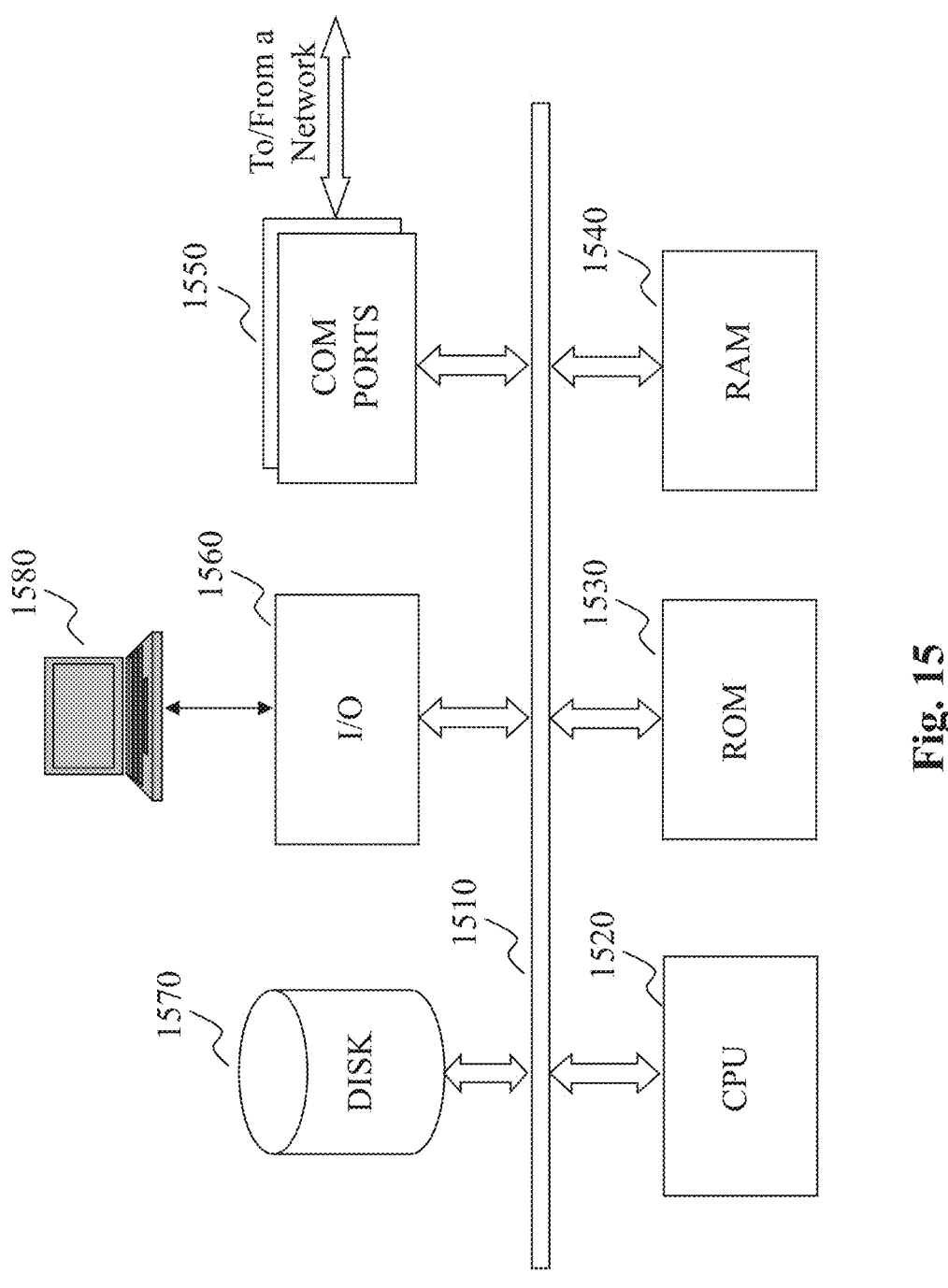
FIG. 15 is an illustrative diagram of an exemplary computing device architecture that may be used to realize a specialized system implementing the present teaching in accordance with various embodiments.

FIG. 15 is an illustrative diagram of an exemplary computing device architecture that may be used to realize a specialized system implementing the present teaching in accordance with various embodiments. Such a specialized system incorporating the present teaching has a functional block diagram illustration of a hardware platform, which includes user interface elements. The computer may be a general purpose computer or a special purpose computer. Both can be used to implement a specialized system for the present teaching. This computer 1500 may be used to implement any component of the preoperative surgical resection planning and simulation scheme, as described herein. For example, the planning and simulation system as disclosed herein may be implemented on a computer such as computer 1500, via its hardware, software program, firmware, or a combination thereof. Although only one such computer is shown, for convenience, the computer functions relating to the planning and simulation system as described herein may be implemented in a distributed fashion on a number of similar platforms, to distribute the processing load.

Computer 1500, for example, includes COM ports 1550 connected to and from a network connected thereto to facilitate data communications. Computer 1500 also includes a central processing unit (CPU) 1520, in the form of one or more processors, for executing program instructions. The exemplary computer platform includes an internal communication bus 1510, program storage and data storage of different forms (e.g., disk 1570, read only memory (ROM) 1530, or random access memory (RAM) 1540), for various data files to be processed and/or communicated by computer 1500, as well as possibly program instructions to be executed by CPU 1520. Computer 800 also includes an I/O component 1560, supporting input/output flows between the computer and other components therein such as user interface elements 1580. Computer 1500 may also receive programming and data via network communications.

Hence, aspects of the methods of preoperative planning and simulation and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, in connection with surgical resection planning and simulation. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the preoperative planning and simulation techniques as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A method comprising:
   receiving, at a computer system, patient data for a patient, wherein the patient requires thoracic surgery;
   generating, via a processor of the computer system, a three-dimensional (3D) computer-rendered inflated thoracic model of the patient using the patient data, the 3D computer-rendered inflated model corresponding to at least one lung of the patient in an inflated state;
   placing, via the processor, a cutting line on the 3D computer-rendered inflated thoracic model, the cutting line representing where a surgeon should cut the patient during the thoracic surgery, resulting in a marked, inflated 3D thoracic model, wherein the cutting line further comprises a ribbon having a width equal to a selected staple cartridge;
   modifying, via the processor, the marked, inflated 3D thoracic model to account for deflation of the at least one lung of the patient, resulting in a marked, deflated 3D thoracic model; and
   displaying, via a display device, the deflated 3D thoracic model.

2. The method of claim 1, wherein the patient data comprises an x-ray image.

3. The method of claim 1, wherein the patient data comprises at least one of a computerized tomography (CT) scan and a magnetic resonance imaging (MRI) scan.

4. The method of claim 1, further comprising:
   placing, via the processor along the cutting line, staple positions,
   wherein the staple positions are displayed via the display device as part of the deflated 3D thoracic model.

5. The method of claim 4, wherein the staple positions are identified during wedge resection planning.

6. The method of claim 1, wherein during the displaying of the deflated 3D thoracic model, thickness of tissue of the patient is conveyed according to brightness, such that a brighter intensity indicates thicker tissue.

7. A system comprising:
   a display;
   at least one processor; and
   a non-transitory computer-readable storage medium having instructions stored which, when executed by the at least one processor, cause the at least one processor to perform operations comprising:
   receiving patient data for a patient, wherein the patient requires thoracic surgery;
   generating a three-dimensional (3D) computer-rendered inflated thoracic model of the patient using the patient data, the 3D computer-rendered inflated model corresponding to at least one lung of the patient in an inflated state;

placing a cutting line on the 3D computer-rendered inflated thoracic model, the cutting line representing where a surgeon should cut the patient during the thoracic surgery, resulting in a marked, inflated 3D thoracic model, wherein the cutting line further comprises a ribbon having a width equal to a selected staple cartridge;

modifying the marked, inflated 3D thoracic model to account for deflation of the at least one lung of the patient, resulting in a marked, deflated 3D thoracic model; and displaying, via the display, the deflated 3D thoracic model.

8. The system of claim 7, wherein the patient data comprises an x-ray image.

9. The system of claim 7, wherein the patient data comprises at least one of a computerized tomography (CT) scan and a magnetic resonance imaging (MRI) scan.

10. The system of claim 7, the non-transitory computer-readable storage medium having additional instructions stored which, when executed by the at least one processor, cause the at least one processor to perform operations comprising:

placing, along the cutting line, staple positions, wherein the staple positions are displayed via the display as part of the deflated 3D thoracic model.

11. The system of claim 10, wherein the staple positions are identified during wedge resection planning.

12. The system of claim 7, wherein during the displaying of the deflated 3D thoracic model, thickness of tissue of the patient is conveyed according to brightness, such that a brighter intensity indicates thicker tissue.

13. A non-transitory computer-readable storage medium having instructions stored which, when executed by at least one processor, cause the at least one processor to perform operations comprising:

receiving patient data for a patient, wherein the patient requires thoracic surgery;

generating a three-dimensional (3D) computer-rendered inflated thoracic model of the patient using the patient data, the 3D computer-rendered inflated model corresponding to at least one lung of the patient in an inflated state;

placing a cutting line on the 3D computer-rendered inflated thoracic model, the cutting line representing where a surgeon should cut the patient during the thoracic surgery, resulting in a marked, inflated 3D thoracic model, wherein the cutting line further comprises a ribbon having a width equal to a selected staple cartridge;

modifying the marked, inflated 3D thoracic model to account for deflation of the at least one lung of the patient, resulting in a marked, deflated 3D thoracic model; and displaying, via a display, the deflated 3D thoracic model.

14. The non-transitory computer-readable storage medium of claim 13, wherein the patient data comprises an x-ray image.

15. The non-transitory computer-readable storage medium of claim 13, wherein the patient data comprises at least one of a computerized tomography (CT) scan and a magnetic resonance imaging (MRI) scan.

16. The non-transitory computer-readable storage medium of claim 13, the non-transitory computer-readable storage medium having additional instructions stored which, when executed by the at least one processor, cause the at least one processor to perform operations comprising:

placing, along the cutting line, staple positions, wherein the staple positions are displayed via the display as part of the deflated 3D thoracic model.

17. The non-transitory computer-readable storage medium of claim 16, wherein the staple positions are identified during wedge resection planning.

18. The non-transitory computer-readable storage medium of claim 13, wherein during the displaying of the deflated 3D thoracic model, thickness of tissue of the patient is conveyed according to brightness, such that a brighter intensity indicates thicker tissue.

* * * * *